(12) United States Patent
Amalaha

(10) Patent No.: US 8,715,344 B2
(45) Date of Patent: May 6, 2014

(54) WHOLLY IMPLANTABLE NON-NATURAL HEART FOR HUMANS

(76) Inventor: Leonard D. Amalaha, Sterling, VA (US)

( * ) Notice: Subject to any disclaimer, the term of this patent is extended or adjusted under 35 U.S.C. 154(b) by 494 days.

(21) Appl. No.: 12/926,117

(22) Filed: Oct. 27, 2010

(65) Prior Publication Data

US 2011/0190880 A1 Aug. 4, 2011

Related U.S. Application Data

(63) Continuation of application No. 12/152,896, filed on May 19, 2008, now abandoned.

(51) Int. Cl.
*A61M 1/10* (2006.01)
(52) U.S. Cl.
USPC .......................................... 623/3.11; 623/3.1

(58) Field of Classification Search
USPC ................................... 623/3.1, 3.11
See application file for complete search history.

(56) References Cited

U.S. PATENT DOCUMENTS

2008/0208333 A1* 8/2008 Shearing .................. 623/3.1

* cited by examiner

*Primary Examiner* — Thomas J Sweet
*Assistant Examiner* — Matthew Schall
(74) *Attorney, Agent, or Firm* — Symbus Law Group LLC; Clifford D. Hyra

(57) ABSTRACT

A wholly implantable non-natural heart for humans includes a pumping unit, a power generating unit, and a controller. An I beam type chassis with matching holes is provided for supporting valve mounting bodies of the non-natural heart.

28 Claims, 8 Drawing Sheets

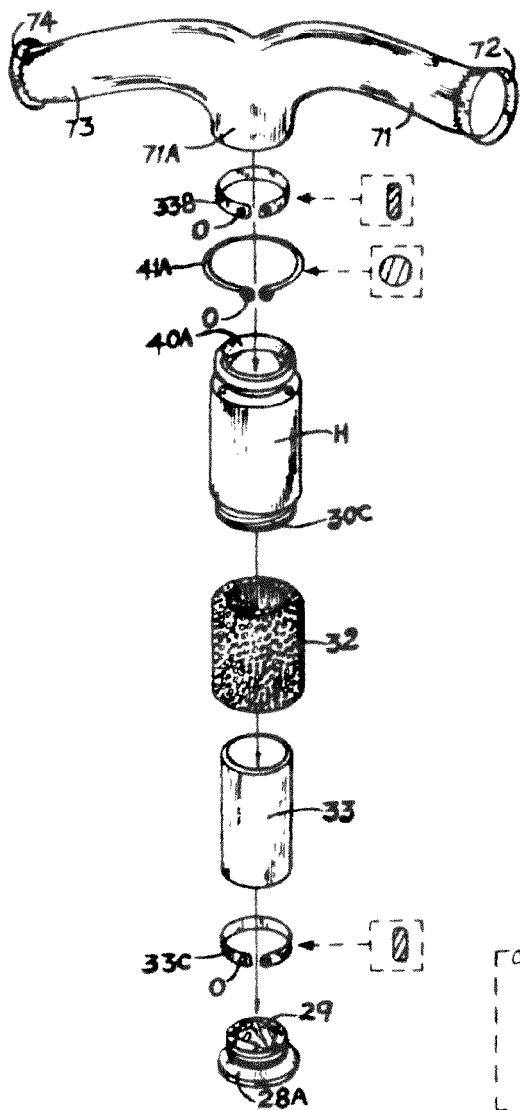
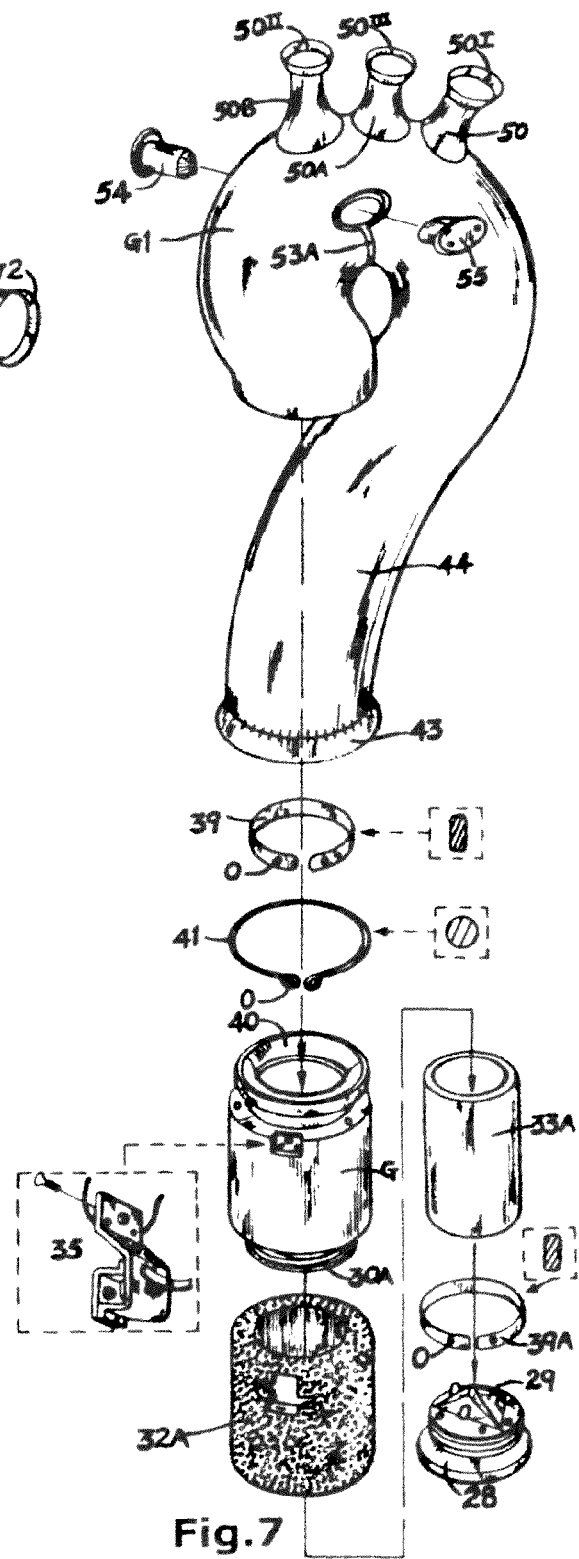
Fig.6
Fig.7

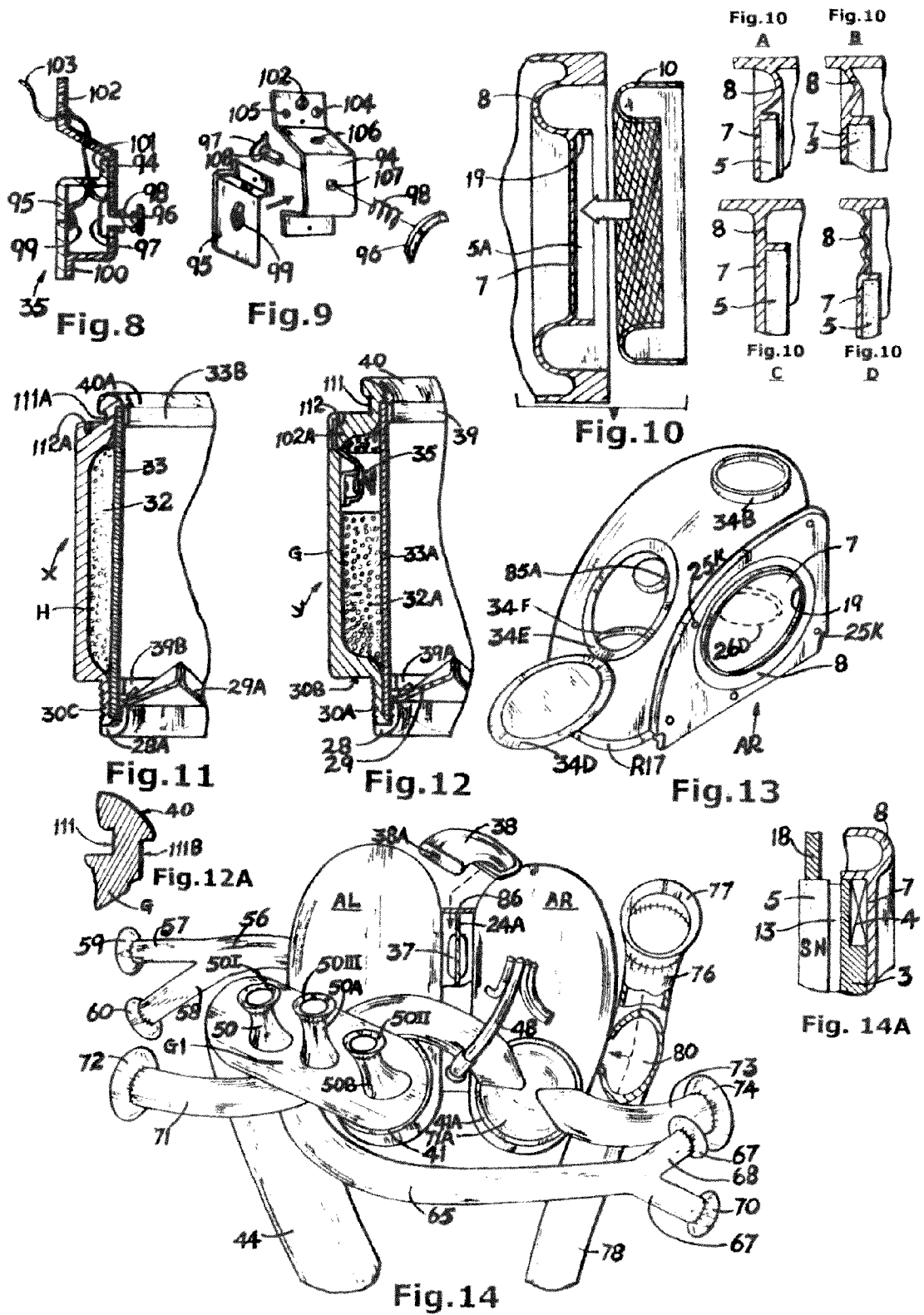

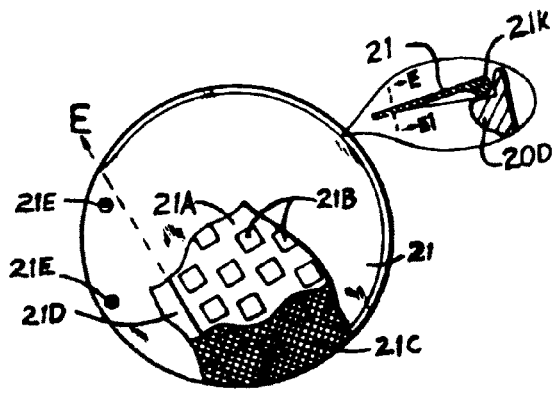
Fig. 35
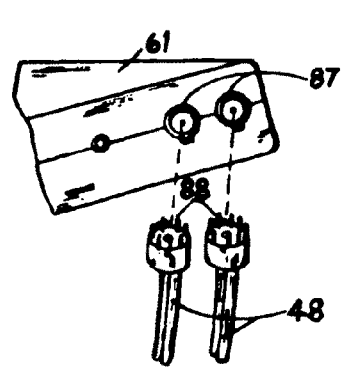
Fig. 42
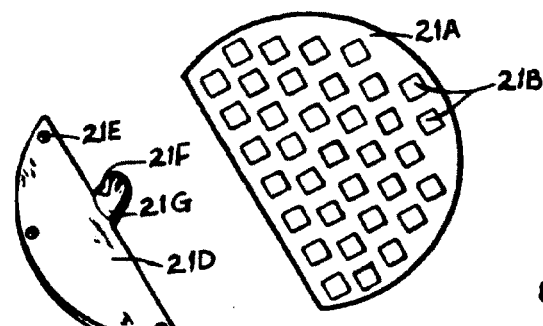
Fig. 36   Fig. 37
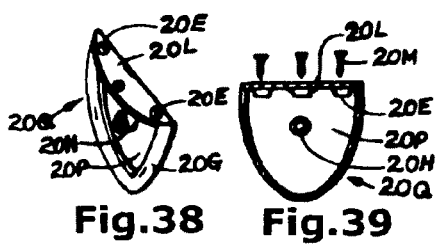
Fig. 38   Fig. 39
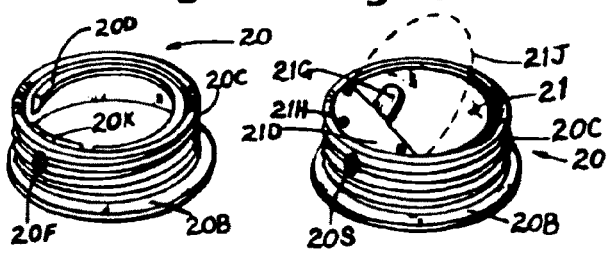
Fig. 40   Fig. 41
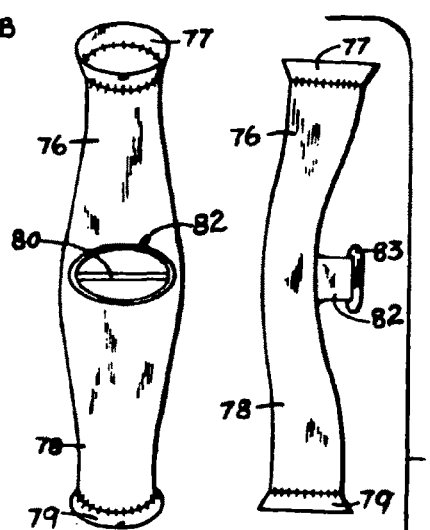
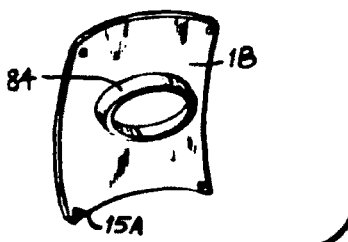
Fig. 43

WHOLLY IMPLANTABLE NON-NATURAL HEART FOR HUMANS

CROSS-REFERENCE TO RELATED APPLICATIONS

This is a continuation of application Ser. No. 12/152,896, filed May 19, 2008 now abandoned, which is incorporated herein in its entirety by reference.

FIELD OF INVENTION

This present invention relates to an artificial heart for humans that is wholly implantable but is specifically, one that has a self-sustaining, redundant, regenerative power supply module that does away with batteries for the purpose of supplying uninterruptible power to solenoid actuators, as well as an electronic control circuit configured in such a manner as to allow the heart to vary frequency and contractile force. The heart, power supply module and the electronic control unit can be made into various sizes such that whole implantation can be made possible in individuals of various body sizes. However, conventional batteries such as rechargeable Lithium Ion may also be employed with periodic replacements. Owing to the complex nature and size of this invention, this application will deal with only the pumping unit I, while the power generating unit II, and controller III will be follow-up applications.

BACKGROUND OF THE INVENTION

Over so many decades man has made valiant efforts to replace completely the natural heart with an artificial one. The Jarvik-7 is one such design. It is bulky, driven by compressed air, and has a wheeled about control unit. It made headlines years ago when it was implanted into dentist, Dr. Schroader, who died after several months. Several improvements have been made on the original design. An Abiocor design was recently approved for trials in humans by the US Food and Drug Administration (FDA). This design showed some promise but was abruptly discontinued when some patients died after the devices unexpectedly failed. Meanwhile, the FDA again approved implantation of this device in some of the weakest heart patients who have less than 30 days to live. The Abiocor, nevertheless, is a considerable improvement over the Jarvik-7 albeit with still a great deal of hurdles to overcome. There have been other attempts to meet this challenge, but with little or no success. Replacing the natural heart with a properly functioning artificial heart that can truly prolong human life is indeed a daunting task.

Several problems plague these aforementioned designs. They include, but are not limited to, bulkiness, difficulty being miniaturized into different sizes to fit individuals of various sizes. They usually do not communicate with the brain as the natural one does via the nerves, and as such do not vary frequency of beats and contractile force among other variables, as well as eliciting life-threatening thrombogenic events. Also, battery size and operating life is another major problem. Ventricular Assist Devices (VAD) have proven effective in some instances, but they only aid the natural heart and are not truly capable of replacing it.

The natural heart with its myriad of capabilities which includes the ability to continuously communicate with the brain, can be considered an "active" pump, while the above aforesaid artificial designs can be classified as strictly "passive" pumps. Essentially, this is the difference between active and passive functionality of natural and man-made body systems.

SUMMARY OF THE INVENTION

It is the primary objective of this present invention to provide a wholly implantable non-natural heart that effectively resolves the major shortcomings of the prior art. This includes as follows: (a) Amenability to miniaturization to various sizes; (b) amenability to current advanced mass production techniques; (c) ability to communicate with the brain via the nerves (sympathetic and parasympathetic); (d) power generator with true long-term reliability that is implanted in the lower abdomen where it can be removed and replaced surgically, easily if need be, without interfering with the heart; (e) Solenoid driven actuators that are easily controlled electronically; (f) an electronic control unit that can be configured in such a manner as to be able to control the solenoid actuators such that they permit the heart to change frequency and contractile force; (g) ability to use temperature and pressure sensors' signals to help vary output; (h) ability to provide functional reliability that is capable of truly prolonging human life.

The above-mentioned capabilities of the present invention are made possible by a wholly implantable non-natural heart system composed of two auricles and two ventricles, each of which is driven by solenoid actuators interacting with high energy permanent magnets . . . said chambers being provided with ejection valves. The aforesaid solenoid actuators are powered by a power generation module designed to be self-sustaining and that can be manufactured cost effectively. The controller amplifies the voltages from the power module and manipulates signals from embedded temperature and pressure sensors as well as utilizing the natural signals from the cardiac/vargus trunks, retrieved via cuff electrodes to modify the output of the solenoid actuators thereby effectively varying ventricular compliance in accordance with bodily requirements. The electronic controller is essentially a modified pacemaker. Various configurations of pacemakers are on the market and their basic control circuit designs are well known art in the field of electronics.

The primary objective, configuration, capabilities and advantages of the present invention will be more readily understood when the following detailed description of an embodiment of the present invention is read in conjunction with the accompanying drawings. The need to keep the weight of a given size of heart within desirable limits, i.e., about 2-3 lbs or less, entails employing materials that are not just bio-compatible, but also of light weight and high strength. High strength aircraft aluminum is preferred for the tubular housings G and H, the chassis 23, the valve coupling bodies 22 and 22A, the coupling plates 1, 1A, 1B and 1C. The material thickness should range from about 1/32" to about 1/8" depending on whether there are varying thicknesses as in the tubular housings G and H. High carbon steel or aluminum can be used for the valve diaphragm inserts 21A, 21D (FIGS. 35) and 29R, 30U (FIG. 30). The valves 20 and 28 are preferably made of titanium, aluminum or nylon.

The valve reinforcing fabrics of choice are nylon and Kevlar. However, other materials with high strength fibers may be used. Newer composite plastic materials that have been certified as bio-inert may also be used to manufacture the components of this present invention.

BRIEF DESCRIPTION OF THE DRAWINGS

FIG. 6 is an exploded view of the components which constitute the pulmonary pulsating system.

FIG. 7 is an exploded view of the components which constitute the aortic pulsating system.

FIG. 8 is a cross-sectional view of the mechanical overpressure switch.

FIG. 9 is an exploded view of the mechanical overpressure switch shown in FIG. 8.

FIG. 10 is a schematic drawing showing how a reinforcing woven fabric mesh is coupled to a yieldable surround.

FIGS. 10A-D represent various possible configurations for the yieldable surrounds which respectively are, a single or double roll concave, single or double V-groove, a flat annular and an integral accordion.

FIG. 11 is a cross-sectional view of pulmonic system components (pulsating unit) according to this present invention.

FIG. 12 is a cross-sectional view of lower aortic system components (pulsating unit) according to this present invention.

FIG. 12A is a close-up view of the upper neck of the housing of the lower aortic system assembly.

FIG. 13 is a perspective view of the auricles configuration according to the teachings of this present invention.

FIG. 14 is a perspective view of the top of this present invention showing pressure equalization vents and ducts.

FIG. 14A represents another embodiment of this present invention constituting a moving coil (MC) configuration as opposed to the moving magnet (MM) system depicted in FIG. 1.

FIG. 35 is a partially cutaway underside view showing lip bulge detail (inset) of a single leaflet valve diaphragm according to this present invention.

FIG. 36 is a view of a stationary leaflet member for a mono-leaflet receiving valve and damping material.

FIG. 37 is a reinforcing movable leaflet member for a mono-leaflet receiving valve in accordance with this present invention.

FIG. 38 is a perspective view of the diaphragm mounting body of the mono-leaflet receiving valve.

FIG. 39 is a cross-sectional view of the diaphragm mounting body shown in FIG. 38.

FIG. 40 is a perspective view of an embodiment of a mono-leaflet receiving valve without the diaphragm mounted.

FIG. 41 is a perspective view of an embodiment of a mono-leaflet receiving valve with the diaphragm mounted on.

FIG. 42 is a diagram showing round connectors for the controller. Other connector designs can also be employed.

FIG. 43 shows design variants of vena cava system members shown in FIG. 23 for the delivery of larger blood volumes.

DETAILED DESCRIPTION OF THE EMBODIMENT

Figure 1:
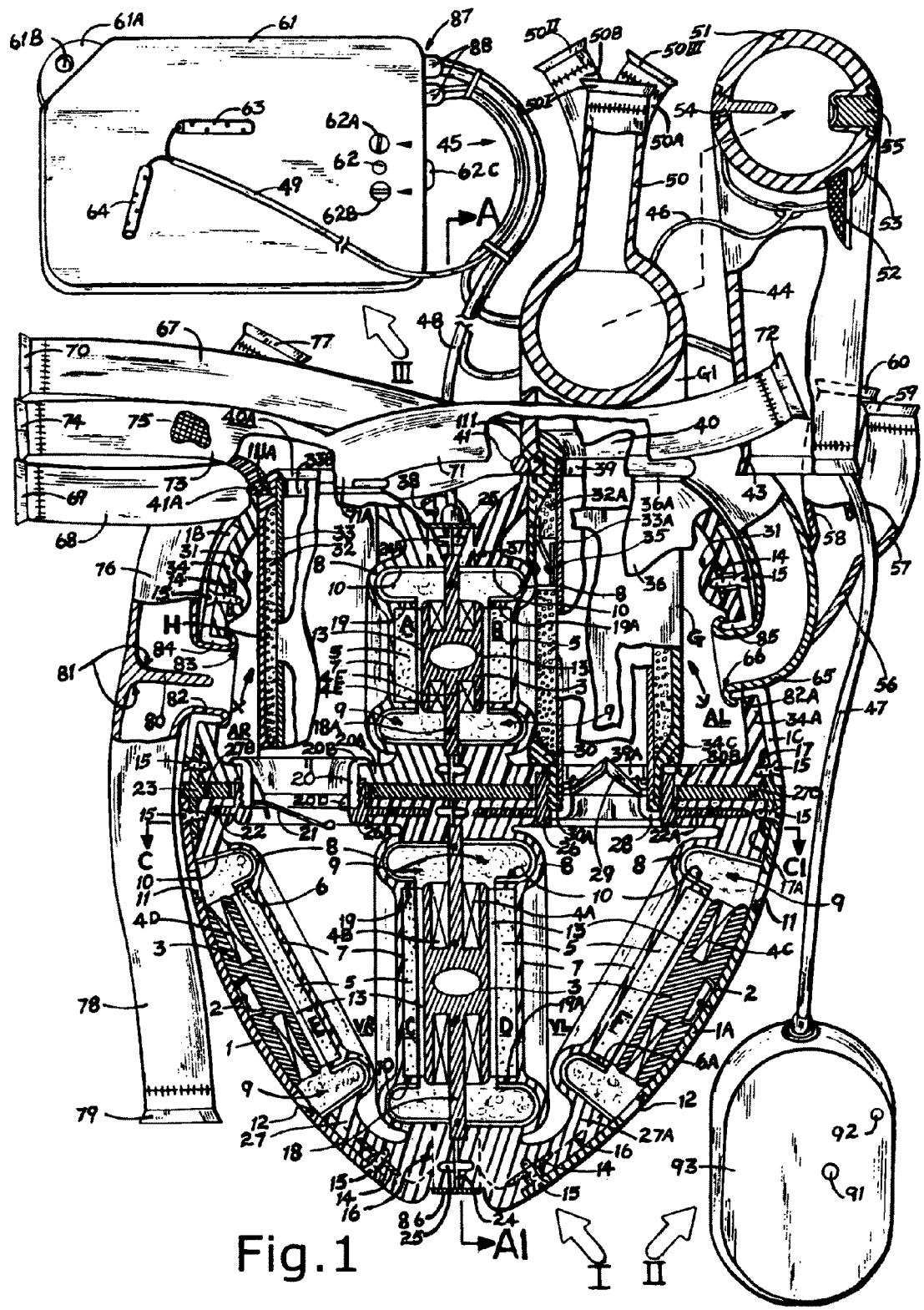
FIG. 1 is a partially cutaway/cross-sectional view showing the components that constitute this present invention.

Close observation of the arrangement of FIG. 1 shows that the chassis member 23 is essentially an I-beam design to provide the desired strength to support the rest of the member components. The thickness of the walls of the surrounds should be made such that they permit rapid axial responses of the moving magnets with varying excursion distances while having the toughness to withstand long service life. This is why reinforcement is very important. Also, true laminar flow is encouraged throughout this design. All valves and mounting components are designed to have no sharp edges that will destroy blood components and set off thrombogenic events. It is desirable as shown in the design and preference of materials of construction that the valves have adequate damping factor on closure so as to reduce the tendency to destroy the blood components.

The iron sheets of the actuators can easily be miniaturized by cutting with lasers. It is possible in the future to utilize MEMS generators embedded in the aorta to take advantage of its significant pulsing to self-power the heart after initiation of pumping action from a jump start external source. Implantation of the power generation unit in the lower abdomen will provide the advantage of access when necessary via a small incision without the risk of interfering with the heart and controller or surrounding organs and structures. This also would permit rapid healing of the wound in the event the power unit is removed and replaced.

Though the natural heart has a difficult and unusual shape to precisely duplicate mechanically, a great deal of effort has been expended here in an attempt to duplicate the pear shape sitting on its apex. This is important in ensuring that it fits properly in the chest cavity around the lungs and other upper body structures. The entire heart can be integrally encapsulated by spraying a thin coat of silicone on its entirety using a spray equipment or brushing it on. It is possible for an individual(s) skilled in the design and/or manufacture of the different components that make up this invention to make reasonable changes for the purpose of increasing system efficiency and reducing costs, without deviating from the basic concepts that govern this present invention.

As shown in FIG. 1, a wholly implantable non-natural heart system for humans is composed of a pumping unit I, a power generating unit II and an electronic control unit III. The pumping unit I, is provided with a mounting chassis 23 in the equatorial direction, upper coupling flange 24 A and a lower coupling flange 24 in the north-south direction. There are also auricle coupling plates 1B and 1C for attaching the vena cava and pulmonary vein systems respectively to the right auricle 34 and left auricle 34A. Unlike with the 34 and 34A, the lower coupling plates 1 and 1A respectively support the right ventricle VR actuating system E and the left ventricle VL actuating system F. A right valve mounting assembly base plate 22 and a left valve mounting assembly base plate 22A are inserts encapsulated by heart material (which is preferably made of silicone), and provided with threaded tubular stems 26A and 26 respectively, for the purpose of connecting valves 20 and 28 in a rigid manner; said tubular stems 26A and 26 passing through matching holes on the chassis 23. There is an upper radial flange 17 and a lower radial flange 17A on the outer diametrical edge of the chassis 23 which serve as mounting posts for the lower edges of the auricle coupling plates 1B and 1C, and the upper edges of the ventricle coupling plates 1 and 1A, by means of screws 15. The opposite ends of said coupling plates, 1B, 1C, 1 and 1A are secured to the surrounding material by means of said screws 15 and inserts 14. The auricle coupling plates 1B and 1C are respectively provided with short tubular inwardly projecting bodies 84, 85 and 85A (FIG. 24) that accept matching tubular projections 82 with lip fold 83, and 65 with lip fold 66 respectively. The tubular lip fold of the vessel 56 (not shown in FIG. 1. See FIG. 24) as aforesaid, like its twin vessel 65 is represented by 66. The inserts 14 are positioned within raised ledge-like projections 31 that protrude into the right auricle chamber AR and the left auricle chamber AL. The vena cava system is an integral configuration that empties into the right auricle AR. The Superior vena cava 76 has a flared entry mouth 77 and exit mouth that empties into the tube 82. The Inferior vena cava 78 has a flared entry mouth 79 and an exit mouth that empties into the aforesaid tube 82. A dividing wall 80 separates the two flows before they empty into the discharge tube 82. Curved surfaces 81 on either side of the wall 80, serve to enhance laminar flow.

The location of the vena cava system 76 and 78 and their coupling plate 1B as shown in FIG. 1 is for clarity purposes only. Their actual location is as shown in FIG. 14. The pulmonary veinous system of the left auricle 34A is a completely separate two-channel configuration. The first channel 65, as aforementioned, has a flared lip 66, which projects into the left auricle AL chamber. The upper section of said channel 65 rises and loops over the top (for clarity) of the left auricle AL, 34A, then bifurcates in the natural manner into the right lung vessels (Pulmonary) 67 with a flared exit mouth 70, and 68 with a flared exit mouth 69. The second channel of the left auricle AL pulmonic vein system 57 is much shorter than the other channel 65 and bifurcates as well into the left lung vessels 54 and 58 which respectively have flared exit mouths 59 and 60. The actuating system of the auricles AR and AL constitutes a centrally located dual coil arrangement having a core 3, and mounting posts 18A and coils 4E and 4F which interact magnetically with flat, oval magnets (preferably neodyminum) 5 rigidly bonded to matching recesses on diaphragms 7 and defined by radial flanges 19 and 19A for the right and left auricles respectively. The diaphragms 7 extend into yieldable surrounds 8 for permitting axial movements of the aforementioned diaphragms as the magnets 5 repel away from the core 3 and coils 4E and 4F, thereby compressing the Chambers AR and AL of the auricles 34 and 34A. Both coils 4E and 4F are simultaneously driven. Strengthening, control and compliance of the surrounds 8 is enhanced by means of meshes 10 (preferably nylon) which are resin reinforced, pressed into shape before being inserted and held in place by bonding with the silicone material to form an integral unit. The walls 34 and 34A of the right and left auricles form into the aforementioned diaphragms 7 and surrounds 8, as well as flat lower ends 20A and 34C provided with cutouts for accepting the edge flanges 20B of receiving valves 20 and mating surfaces 30B of valve coupling assemblies 30A of both aortic G and the pulmonary H circulatory systems' pulsating units, as well as tubular stems 26 and 26A. A thin sheet of resilient foam material 13 is bonded to the face of each side of the core material 3 confronting the magnets 5, for damping. The left auricle inner wall 34A and the right auricle inner wall 34 each bonded to the upper coupling flange 24A which is provided with pins 25 that fit into matching holes on said coupling flange 24A, thereby joining the auricles together as an integral unit. Heat absorbing material 9 is inserted into the cavity created by surrounds 8 to help absorb some of the heat generated by the coils 4E and 4F. Heat from this cavity is vented through grooves 37 that connect to a duct 38 bonded to the top of the heart and within the central groove. The aortic pulsating unit Y is configured in such a manner as to pulse rhythmically with each contraction, thereby increasing the overall performance of the system as occurs with the natural heart. The said system Y is composed of an exterior casing of housing G made preferably of aluminum or any Bio-compatible material such as nylon, Tygon, etc. It has a short grooved neck 111, for accepting the lower edge of an aortic arch G1 and a tension clamp 41. The outer diameter of the neck 111 is narrower than that of the housing G. The inner upper edge of the neck 111 has a smooth curved surface 40 to enhance laminar flow. A recessed inner edge 113 (FIG. 12) is configured to accept the upper edge of a stretchable membrane 33A and a tension retaining clamp 39. The lower edge of the housing G has a tubular threaded neck 30A with an exterior diameter smaller than that of the housing G such that it mates with a threaded inner diametrical edge 26H of a valve mounting body 26. A recessed edge 30B clamps down, sandwiches auricle lower edge material of 34C of auricle body 34A tightly onto upper edge of valve coupling body 26. The lower edge of aforesaid threaded tube 30A is also threaded in such a manner (see FIG. 10) as to accept an aortic ejection valve 28 provided with leaflets 29. The lower edge of the aforementioned stretchable membrane 33A is bonded to the inner diameter of tube 30 and also held securely by a tension retaining clamp 39A. Sandwiched between the membrane 33A and the housing G is a resilient foam backing 32A to permit pulsing or recoils of the said membrane 33A during beats. Also sandwiched between the membrane 33A and housing G is an overpressure switch 35 which is bolted to the upper edge of the housing G.

The curved inner lower surface 30 of the housing G is matched by the shape of the foam backing 32A. In the event of excessive pressure, the switch 35 would be closed so as to introduce great electrical resistance into the controller III's circuit and limit the amount of current drawn by the solenoid actuators' coils 4A, 4B, 4C, 4D, 4E and 4F. The pressure switch 35 in conjunction with an active pressure transducer 55 presents a redundant safeguard against excessive pressure fluctuations. Union of upper edge of valve coupling body 26, recessed edge 30B of housing G and lower edge of heart material 34C presents a tight seal that prevents blood in the left auricle chamber AL from leaking into the left ventricle VL. The aortic arch G1 has a lower edge coupled to the upper neck 111 of the pulsating unit's housing G by means of the tension clamp 41. At the top of the aortic arch G1 sit three integrally formed vessels, branchiocephalic trunk 50B, left common carotid artery 50A and left subclavian artery 50 having respectively, flared exit mouths, 50II, 50III and 50I. On either side of the aortic arch G1 is positioned, a temperature sensor 54 and the pressure transducer 55 which send signals to the controller III via the wires 46 and 53. The cross-section 51 of the aortic arch G1 shows a thickness at its maximum that reduces towards the descending aorta 44, then terminates into the flared mouth 43. On the left pulmonary artery 73, and descending aorta 44 are shown reinforcing meshes 75 and 52 respectively for strengthening the vessels in the traditional manner by midway insertion.

The pulmonary pulsating unit X serves to permit pulsing of the system so as to enhance the overall compliance of the system with each beat. It is composed of a housing H made preferably of aluminum alloys or any bio-compatible material such as nylon, Tygon etc. The outer edge like that of the housing G of the aorta pulsating unit Y is preferably highly polished and/or coated with an anticoagulant to keep blood platelets within the auricles AR and AL from sticking to the said surfaces. The said pulmonic pulsating unit's housing H has an upper neck MA having an outer diameter smaller than that of the body of the housing H and provided with a groove for accepting the lower radial edge 71A of the pulmonary arteries 71 and 73 and held firmly thereon by means of the tension spring 41A. The inner upper edge of the neck IIIA has a smooth curved surface 40A to enhance laminar flow. As with the aortic system, a recessed inner edge is configured to accept the upper edge of a stretchable membrane 33 and a tension retaining clamp (spring) 33B. There is a resilient foam backing 32. The configuration of the lower section of the pulmonic pulsating unit X mirrors that of the aortic system Y and shares the same type of ejection valve 28 provided with three leaflets 29. Where the short tubular edges 36A and 34B of the upper sections of the left and right auricle walls 34A and 34 respectively meet their pulsating unit housings G and H, they are tightly bonded thereon such that no leaks occur during auricle contractions. The aforementioned flared ends of the artificial heart vessels serve to permit their proper attachment to natural vessels of varying diameters. The flares can be integral with the rest of the vessels or they can be made of dacron fabric which may be stitched on, and/or firmly attached to the vessels by bonding.

The left ventricle VL and the right ventricle VR are each driven by a pair of solenoid actuators D,F and C,E respectively. The actuators D and F of the left ventricle VL are larger and more powerful than C and E actuators of the right ventricle VR. However, as can be seen, both actuating systems are essentially of the same configuration. As with the auricles, the ventricles' inner actuators C and D share a common core 3 and mounting posts 18 and actuating coils 4A and 4B which interact magnetically with flat, oval magnets (preferably neodymium) 5 rigidly bonded to matching recesses on diaphragms 7 and defined by radial flanges 19 and 19A for the right and left ventricles respectively. As with the auricles, the diaphragms 7 extend into yieldable surrounds 8 for permitting axial movements of the aforementioned diaphgrams as the magnets 5 repel away from the core 3 and coils 4A and 4B, thereby compressing the chambers VR and VL of the ventricles 27 and 27A. Again, as aforementioned, strengthening, control and compliance of the surrounds 8 is accomplished by means of meshes (preferably nylon) which are resin reinforced, molded into shape before being sandwiched and held in place by bonding with the silicone material to form an integral unit. The cavity created by the surrounds 8 of the central core assembly 3 as aforesaid, is filled with heat absorbing material 9 to absorb some of the heat generated by the coils 4A and 4B. Venting of air within said cavity is via slots 16, to free air in the central dividing groove which is defined by the belt 86, which is used to tie up the left and right sides of the heart by bonding with a desirable bonding agent.

Figure 25:
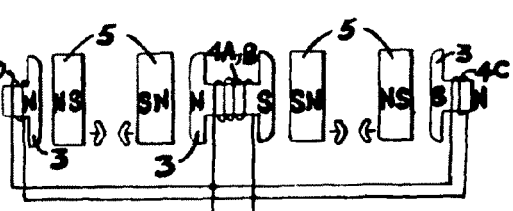
FIG. 25 is a diagram showing proper magnetic polarity orientation of the actuating drive units.

The flat upper walls 27C and 27B of ventricles VR and VL are separated by the lower coupling flange 24. The perforated flange section of valve mounting insert base plates 22 and 22A (see FIG. 15) are rigidly integrally insert molded to said flat upper walls 27C and 27B of said ventricles VR and VL. After the left ventricle VL and right ventricle VR have been rigidly coupled to the lower coupling flange 24 to form an integral unit, the arrangement is then connected to the lower surface of the chassis 23 such that as aforementioned, the threaded tubular stems 26A and 26 pass through matching holes on said chassis 23 as well as through aforesaid flat upper walls 27C and 27B, respectively. The body masses 27 and 27A of the ventricles VR and VL respectively form into the diaphragms 7 and the surrounds 8 as well as the flat upper walls 27C and 27B are provided with hole cutouts (see FIG. 15) for accepting the threaded tubular stems 2G, 26A, 26B and 26C. This arrangement connects the ventricles VR and VL to the auricles AR and AL via the valves 20 and 28. The outer ventricle actuators E and F, like the inner actuators C and D have flat oval magnets 5 (preferably neodymium) rigidly bonded to matching recesses on the diaphragms 7 and defined by radial flanges 6 and 6A for the left and right ventricles respectively. The cores 3 and the actuating coils 4C and 4D of the outer ventricle actuators respectively, are mounted on coupling plates 1 and 1A by means of canted studs 2 that fit snugly onto matching slots on the backs of the said cores 3 and also bonded to the coupling plates 1 and 1A thereon. The aforesaid coupling plates 1 and 1A are connected to the chassis 23 by means of screws 15 at the upper edges and to metal inserts 14 by means of screws 15 at the lower edges. The cavity created by the surrounds 8 are filled with a heat absorbing material 9 for the purpose of absorbing some of the heat generated by the coils 4C and 4D. Venting of air in the said cavity is accomplished via holes 11 and 12 beside the coupling plates 1 and 1A into free air. The drive magnets 5 magnetically interact with the solenoid actuating coils 4C and 4D in such a manner that said drive magnets 5 repel away from the cores 3, thereby compressing the chambers of ventricles VR and VL and forcing the valves 28 of both the aortic Y and pulmonic X systems to open and eject their blood contents into the body. As aforementioned, a thin resilient foam Material 13, bonded to the upper faces of the cores 3, confronting the drive magnets 5 provides damping of force during excursions as the said drive magnets 5 return to their resting positions. Both pairs of actuators D,F and C,E are programmed to actuate simultaneously. Proper magnetic orientation of the solenoids and permanent magnets is shown in FIG. 25.

A wire harness 45 connects the pumping unit I with the power module II, the controller III and the two branches of nerve connecting electrode cuffs 63 and 64 for sympathetic and parasympathetic trunks and temperature 54 and pressure 55 sensors. Wires 46 carry signals to and from sensors 54 and 55, wires 47 connect to the power module II, wires 88 connect to the actuators of the pumping unit I, wires 49 connect to the nerve electrodes 63 and 64. All signals are processed by the controller III which receives the wire harnesses 45 via the plugs 88 and sockets 87 arrangement. The controller is provided with a casing 61, a securing flange 61A with a hole 61B, a power on LED 62 sentinel cord and a pair of power on/off switches 62A and 62B of the screw type preferably. A detailed description of the control circuit will be discussed in a separate patent application.

The dome shape of the upper sections of the auricles 34 and 34A significantly increases the mechanical strength during increased blood pressures while the coupling plates 1B and 1C help to reduce unwanted stretching of the exterior chamber walls. On the other hand, the dome shape of the exterior walls of the ventricles 27 and 27A and the coupling plates 1 and 1A present a considerably stable platform to withstand the much greater dynamic mechanical output excursion vibrations of the actuator's moving magnets 5.

Both receiving valves 20 and ejection valves 28 are designed such that their respective diaphragms 21 and 29 are self closing. However, owing to the fact that the ventricles are working against gravity, the aforesaid diaphragms 29 of the ejection valves 28 should be designed to require much less pressures in the ventricles to open than the leaflets 21 of the receiving valves 20. The said leaflets 21 should be able to open slightly (agape) under the blood load within the auricles AL and AR, even before the solenoid actuators A and B can fire and compress the volume of the chambers and empty a larger blood volume into the ventricles. This is thanks to gravity. However, when the ventricle actuators C,D,E and F activate, compressing their respective chambers and open the aforesaid ejection valves, the receiving valves should completely close.

The temperature probe 54 extends into the aorta and physically contacts blood. It should therefore be preferably made of either titanium or stainless steel. The pressure transducer 55 is shrouded by an integral thinned cross-section of the aortic material so as to enable it to sensitively sense pressure fluctuations without any physical contact with the blood. Standard micro temperature probes and pressure sensors are now cheaply manufactured by various manufacturers.

Figure 2:
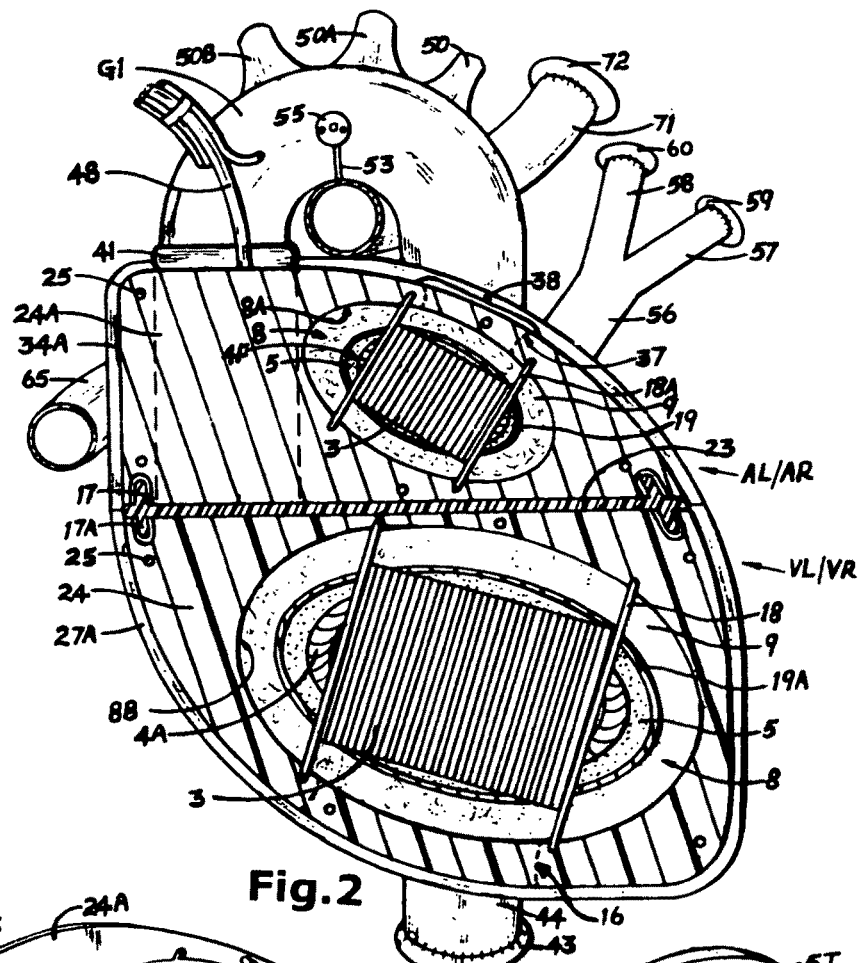
FIG. 2 is a cross-sectional/perspective view of an embodiment of the present invention, taken along line A-A1 of FIG. 1.

As shown in FIG. 2, the auricle chambers AR and AL are provided with an upper coupling flange 24A. Having pins 25, recesses 24B (see FIG. 3) that accept an upper radial flange 17 of the chassis 23; said chassis having as well, a lower radial flange 17A also for the purpose of accepting matching recesses (see FIG. 4) on a lower coupling flange 24; said coupling flange having pins 25. Both the auricle chambers AR/AL and the ventricle chambers VR/VL are provided with oval yieldable surrounds 8 with exterior diametrical edges that match oval cutouts 8A and 8B on the aforesaid coupling flanges 24A and 24 respectively. The inner diametrical edges of the yieldable surrounds 8 form into radial flanged recesses 19 and 19A for accepting matching flat, oval high energy magnets 5 (preferably neodymium); said magnets interacting with the solenoid actuators having coils 4A and 4F wound on cores 3 (preferably sheet type), said cores being rigidly attached to mounting posts 18 and 18A by riveting and/or bonding with a resin. The mounting posts 18 and 18A, fit into matching slots 18C and 18B on their coupling flanges 24A and 24 and are bonded thereon (see FIG. 3 and FIG. 4). This arrangement allows the magnets 5 to repel away from the cores 3 when current flows in them, thereby moving the diaphragms 7 (FIG. 1) and compressing the chambers and forcing the blood in the great vessels 33A (Aortic) and 33 (Pulmonic).

55 represents the temperature sensor which receives current via from the wire harness 48 and running through the groove 53. The clamp 41 firmly secures one end of the aortic arch G1 to aforementioned pulsating unit's housing. The yieldable surrounds 8 connects to flanges 19 for accepting moving magnets 5. Heat absorbing material 9 is disposed within said surrounds 8.

As can be seen, one branch of the pulmonary arteries 71 passes under the aortic arch G1 of the aortic system Y which has branches 50, 50A and 50B representing left subclavian artery, common carotid artery and branchiocephalic trunk respectively, atop said aortic arch. The lower edge of the aortic arch G1 meets the short tubular edge 36A of the upper section of the left auricle 34A and are both firmly attached and waterproofed to the housing G of the pulsating unit X (See FIG. 1 or FIG. 7). The descending aortic vessel 44 is provided with a flared exit mouth 43. The left pulmonary artery 71 is also provided with a flared exit mouth 72. The left pulmonary vein 56 bifurcates in the natural manner into the vessels 57 and 58 having flared exit mouths 60 and 59 respectively. The right pulmonary vein 65 and aforesaid left pulmonary vein 56 are both attached to the left auricle AL and return oxygenated blood from the lungs.

Heat absorption from the coils 4B and 4E is enhanced by insulation material 9 inserted into the surrounds 8. Venting of warm air from the coils is through the slots 37 and duct 38 provided with a curved exit mouth for the two auricles and via the slots 16 for the median ventricle actuators' core 3 into free air. Though the aforesaid right pulmonary vein 65 is shown to rise above the heart in FIG. 1, this is intended for clarity. As shown in FIG. 2, said vein 65 loops around the heart in the usual manner.

Figure 3:
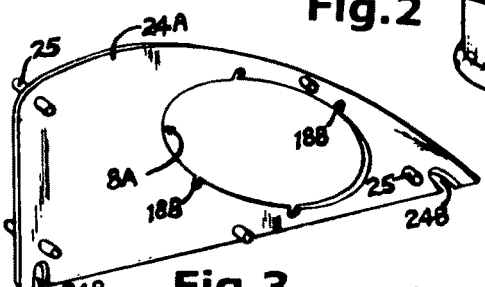
FIG. 3 is a perspective view of the upper chambers' (auricles) coupling flange.

Referring now to FIG. 3, 24A represents the upper coupling flange provided with securing pins 25, chassis recesses 24B and actuator mounting slots 18B and matching surround oval cutout 8A.

Figure 4:
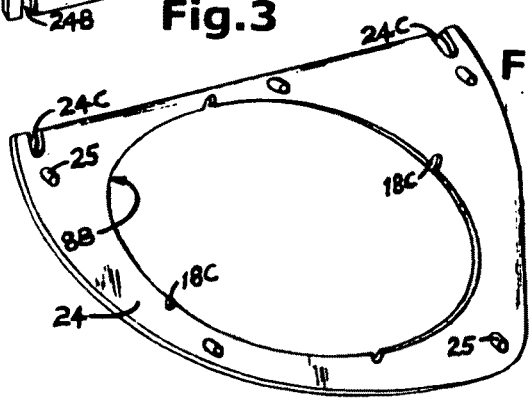
FIG. 4 is a perspective view of the lower chambers' (ventricles) coupling flange.

Referring now to FIG. 4, 24 represents the lower coupling flange provided with securing pins 25, recesses 24C for the chassis flange, actuator mounting slots 18C and oval matching cutout 8B for surrounds.

Figure 5:
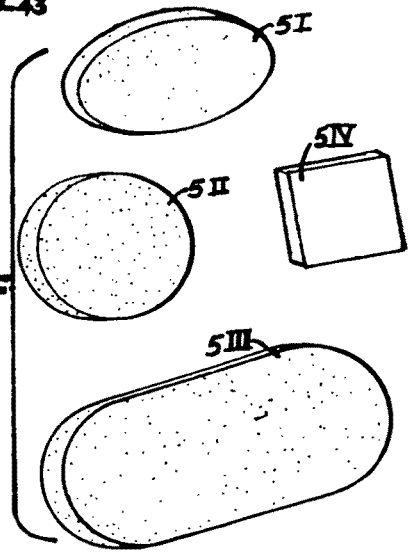
FIG. 5 shows the perspective views of four preferable magnet designs, oval, round, race track and square respectively that can be employed in this present invention.

In reference to FIG. 5, 5I represents a flat oval magnet design employed in this present invention. 5II is a round flat magnet that can be employed in this invention. 5III is another magnet of flat racetrack design that can also be employed in this present invention, 5IV shows a square design. All the magnets shown are preferably made of high energy neodymium. However, other magnet materials of appropriate strength may also be employed.

Referring now to FIG. 6, the ejection valve is represented by 28A which has three leaflets 29. The said ejection valve 28A has a threaded outer diameter for coupling to the lower edge of the pulsating units' housing H. The lower threaded edge 30C of said housing H couple to tubular stems. 40A represents the polished curved upper lip for promoting laminar flow. 33 represents a stretchable membrane while 32 is the yieldable foam backing. 33C, 41A and 33B are the tension springs for attaching the membrane 33 and the pulmonary trunk 71A to the housing H. The pulmonary trunk 71A bifurcates into the arteries 71 having a flared exit mouth 72, and vessel 73 having the flared exit mouth 74. The aforesaid tension springs 33C, 41A and 33B have rounded cross-sections to prevent damage to the said membrane 33, and also to keep blood platelets from being destroyed and resulting in thrombogenic events. They also have openings 0 to aid in positioning.

Referring now to FIG. 7, 28 is an ejection valve provided with leaflets 29. The tension springs 39A and 39 are used to couple the stretchable membrane 39A to the pulsating housing G which has an upper smooth and curved surface 40 to improve laminar flow. 30A represents the threaded lower edge of the housing H for coupling to a tubular stem. 32A represents a yieldable foam backing for the membrane 33A. 35 represents the overpressure switch for controlling excess pressures. The tension spring 41 is used to attach the aorta G1 to the housing G. The descending aorta 44 has a flared exit mouth 43 for attaching to natural tissues of various sizes. 50 represents the left subclavian artery, while 50A represents the common carotid artery. The branchiocephalic trunk is represented by 50B. The flared exit mouths 50I, 50II and 50III are for attachment to natural vessels. The groove 53A carries wires to temperature 54 and pressure 55 sensors. Also, the tension springs 39A, 41 and 39 have rounded cross-sections to prevent vessel and/or blood platelet damage that may lead to thrombosis or clots. The openings 0 on the aforesaid springs aid in positioning.

Referring now to FIG. 8, the number 35 represents the overpressure switch having a bottom nonconducting piece (preferably plastic) 95, and a metal top piece 95. Wires 103 are passed through holes on the bottom piece 95 and top piece 94 to a non-moving contact 99 and movable contact 97 respectively. Sandwiched between the top piece 94 and a stop 96 which is rigidly connected to a stem on the upper contact 97, is a return spring 98, the aforesaid stem passing through a hole on the top plate 94 for permitting axial movements of the movable contact 97. A hole 102, is used to mount the switch to the housing.

The overpressure switch as shown in FIG. 1 is a simple cantilever contact switch design that is cheap and easy to make. However, the micro-switch depicted in FIG. 8 though more complex and more expensive, permits more accurate axial movements which engender a greater safety factor and reliability.

Referring now to FIG. 9, the bottom plate 95 has a contact point 99 while the top plate 94 has the square hole 107 for accepting the stem 108 of the upper contact 97 which passes through the return spring 98 and is rigidly attached to the stop 96. Wires are passed through holes 104, 105 and 106 to the contacts 97 and 99. Representing the mounting hole is 102.

Referring now to FIG. 10, the magnet housing 5A is defined by the radial flange 19. The diaphragm 7, forms into a yieldable surround 8 which permits axial motions of said diaphragm 7. The woven/molded reinforcing mesh 10 is preferably made of nylon, Kevlar, carbon-carbon fibres or other tough material that when bonded to the movable members, considerably increases toughness and compliance.

Referring now to FIGS. 10A-10D, as aforementioned, these figures represent possible yieldable surround configurations for the diaphragms 8 as further embodiments of this invention. FIG. 10A shows a single or double roll concave. FIG. 10B shows a single or double V groove. FIG. 10C shows a flat annular design while FIG. 10D is an integral accordion design. In FIGS. 10A through D, 8 as aforesaid represents the yieldable surrounds which are integral with the diaphragms 7 having the moving magnets 5 attached to them preferably by bonding with a suitable bonding agent.

In reference to FIG. 11, H represents the housing of the pulmonary pulsating unit X, provided with a recessed neck 111A which is provided with a smooth, curved upper edge 40A. There is a lower threaded outer edge 30C for coupling to the right ventricle. Owing to the fact that the tubular housing G and H of the pulsating units Y and X sit inside the auricle chambers and do have considerably large surface areas in direct contact with blood their surfaces should be highly polished and/or coated with anti-coagulants or encapsulated with a thin coat of silicone.

Referring now to FIG. 12, G represents the housing for the Aortic system's pulsating unit Y having a recessed upper neck 111 provided with a curved smooth surface 40 and a lower threaded outer neck 30A for connecting to the left ventricle. 33A represents the stretchable membrane having a yieldable foam backing 32A. The upper edge of the membrane is attached to the inner side of the neck 111 by bonding, as well as with the tension retaining spring 39. The lower edge of the membrane 33A is also attached to the inner opposite side of the threaded edge 30A by bonding, as well as with the tension retaining spring 39A. The ejection valve 28, has leaflets 29 and is rigidly connected to the matching opening on the radial inner diametrical edge of aforesaid threaded lower neck 30A. 112 represents small holes for mounting the unit unto the ventricles by means of a special tool. Overpressure during operations is controlled by the switch 35 which closes contacts if overstretching of the membrane 33A should occur. A screw 102A firmly holds it to housing G.

The resilient backing material 32 or 32A for stretchable membranes 33 and 33A respectively for the pulmonary and aortic pulsating systems X and Y can be of any foam rubber which would not give off gas that may permeably seep into the blood stream and result in immune system responses. The stretchable membranes 33 and 33A should be non-blood permeable. A material such as latex or silicone rubbers may be used. It may also be possible to employ some biocompatible woven stretch fabric materials. However, it is not desirable that blood should penetrate this membrane to the backing material, as this may provide a hiding place for dead blood cells that may initiate adverse thrombogenic events in the system. Refering again to FIG. 11, 33 represents an aforesaid stretchable membrane provided with a yieldable foam backing 32; said membrane 33 being attached to the upper and lower edges of said housing H by bonding, as well as with the tension retaining springs 33B and 39B. An ejection valve 28A having leaflets 29A is rigidly connected to the matching opening on the radial inner diametrical edge of the aforesaid threaded lower edge 30B. Holes 112A are for mounting the unit into a right ventricle using a special tool.

Referring now to FIG. 12A, G represents the housing of the aortic pulsating system Y having a recessed neck 111 for connecting to the aortic arch G1. 111B represents a recessed edge for attaching the upper section of a stretchable membrane (see FIG. 12), while 40 represents the smooth curved surface for improving laminar flow. The pulmonic system X is of a similar arrangement.

In reference to FIG. 13 which is the right auricle AR, which is similar in construction to the left auricle AL, 7 represents the movable diaphragm having an integral yieldable surround 8, connected to a radial edge flange 19 for bondably retaining a moving magnet that matches and mates with the inner diametrical circumference defined by said flange 19. Holes 25K are positioned on the mating face for the purpose of accepting holding pins on an upper coupling flange (FIG. 3). 34B represents a short neck flange for connecting the Aorta to the auricle by means of a retaining spring clamp. The opening defined by said neck flange 34B is in the same line of sight with a second opening 26D on the lower bottom surface which accepts the pulmonary pulsating unit X (FIG. 11) and its ejection valve 28A. 85A represents a hole for positioning the vena cava system members 82 and 84 of FIG. 1. A second opening 34F is for mounting a single leaflet receiving valve 20 of FIG. 41. A lid 34D is preferably cut out as a flap with a beveled oval profile defining a hole 34E positioned in the same line of sight as the aforesaid opening 34F for the purpose of easily mounting the aforementioned receiving valve 20. After mounting of the aforesaid valve 20 is completed the said lid 34D is reattached by means of bonding and/or stitching to present an effective seal. R17 represents a matching recess for the upper flange section 17 of the chassis 23 of FIG. 1. Beveling of the cutout 34E increases surface area for bonding.

In reference to FIG. 14 which is a perspective view of FIG. 1 seen from the top, AR and AL represent the right and left auricles respectively. G1 represents the aortic arch with the vessels 50, 50A and 50B for supplying blood to the upper part of the body. 44 represents the descending aorta for supplying blood to the lower parts of the body. 78 represents the inferior vena cava. Owing to the difficulty of duplicating exactly the shape of the natural heart, both the vena cava and the aortic vessels are not in their exact natural locations. However, when the vessels are made substantially long, they should easily connect to the natural ones with little or no problems. 71 and 73 represent the left and right pulmonary arteries respectively. 65 represents the right pulmonary vein which bifurcates into the vessels 67 and 68 that supply oxygen rich blood to the right lungs.

56 represents the left pulmonary vein which also bifurcates into the vessels 57 and 58 which supply oxygenated blood to the left lung. 48 represents a branch of the wire harness that runs from the controller to the actuator coils. 37 represents the air channels that connect to the duct 38 which has an exit mouth 38A for supplying cool air to the actuator coils of the auricles and venting warm air during actuations. 86 represents the belt for increasing the strength of the attachment of the left and right sides of the heart. It should be noted that because of the twists and bends of the natural heart's vessels, the right pulmonary artery 73 slips under the aortic arch. However, with the present invention, the left pulmonary artery 71, is the one that slips under the aortic arch G1. The descending aorta 44, as with the natural heart descends the left side walls of the left auricle AL and left ventricle VL respectively.

Referring now to FIG. 14A, 8 represents a yieldable surround integral with a movable diaphragm 7 with a coil 4 wound on an iron core 3. 13 represents a damping material while 5 represents the magnet. 18 represents a means for positioning the magnet 5 within the heart material.

In proof of concept trials, both moving magnet (mm) and moving coil (mc) actuators have proven capable of producing enough repulsive forces necessary to overcome high resistive loads as can be presented by large individuals at sea level. Mobile 10W-40 grade engine oil was used as the driven fluid because its viscosity profile approximates that of blood which is higher than that of water. A single leaflet prototype valve was used in the trials. No oscillator circuit was used to control switching of the solenoids. However, rapid manual on/off operation of the contact switch produced rapid responses of the solenoids and effective opening of the valve. After more than 3600 operations of the two types of actuators, the following conclusions were reached: The moving magnet had a slight drop in power as the temperature of the actuating coils increased However, owing to the fact that the moving magnet and diaphragm have no continuous physical connection with the coils, the oil stayed essentially cool. This is advantageous because the actuators should not heat up the blood. The moving coil system on the other hand had a cooler coils temperature owing to the fact that during excursions, air was used more effectively as a means of cooling. However, the oil showed more increased warmth than with the moving magnet system apparently because the coils conducted heat through the diaphragm into the oil with time. It will now be emphasized that I believe that the shortcomings of either system can easily be overcome by utilizing the right materials of construction. Also, in the fully implanted and functioning design, there will be the normal bodily conduction and removable of heat that through the lungs, which will further drop blood temperatures to appropriate levels.

Figure 15:
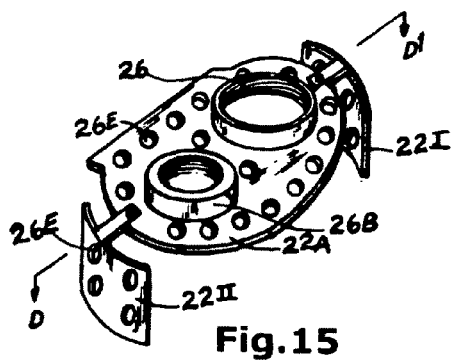
FIG. 15 is a perspective view of a valve mounting body assembly shown in FIG. 19.

Referring to FIG. 15, the valve mounting assembly base plate 22A for the left ventricle has perforations 26E to allow the molding material to flow through and present an integral interlocking unit. Reinforcing inserts 22I and 22II are riveted to the base plate 22A and are also provided with perforations 26E. Tubular valve mounting bodies 26 and 26B are integral with the base plate 22A.

Figure 16:
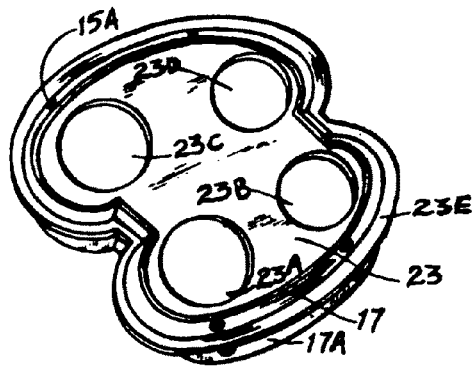
FIG. 16 is a perspective view of the chassis assembly for coupling upper (auricles) and lower (ventricles) members according to this present invention.

Referring now to FIG. 16, the chassis 23 is provided with mounting holes 15A on upper and lower parts of flanges 17 and 17A. 23A, 23B, 23C and 23D represent the matching holes for the tubular valve coupling bodies shown in FIG. 15.

Figure 17:
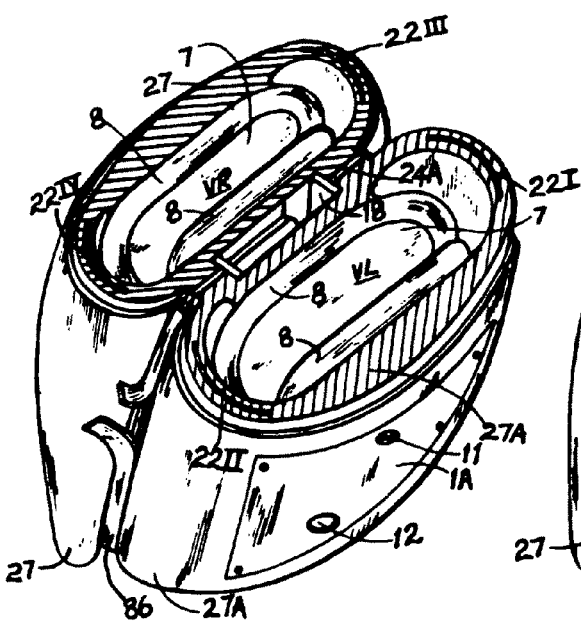
FIG. 17 is a partially cutaway view from the top, of ventricles' configuration taken along line C-C1 of FIG. 1.

In reference to FIG. 17, the top layers of left ventricle VL and right ventricle VR, are cut off (taken along line C-C1 of FIG. 1) for greater detail. 27 and 27A represent the left and right walls of the ventricles. 22III and 22IV represent the reinforcing inserts while 8 represents yieldable surrounds for diaphragms 7. The mounting posts for actuator solenoids are represented by 18. The left ventricle's VL outer actuator coupling plate 1A is provided with air vent holes 11 and 12. A reinforcing belt 86 ties both halves of the heart together. 22I and 22II are reinforcing inserts.

Figure 18:
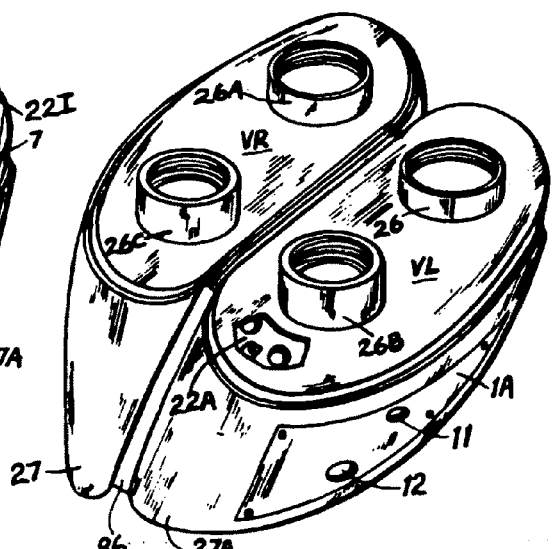
FIG. 18 is a perspective view of the ventricles' assembly showing the tubular valve mounting stems.

In reference to FIG. 18, the right land left walls of the ventricles are represented by 27 and 27A respectively. VR represents the right ventricle provided with valve mounting bodies 26A and 26C. The left ventricle VL is provided with valve mounting bodies 26 and 26B and coupling plate 1A which has air vents 11 and 12. The strengthening belt is represented by 86. 22A represents the base plate insert for the aforesaid valve mounting bodies.

Figure 19:
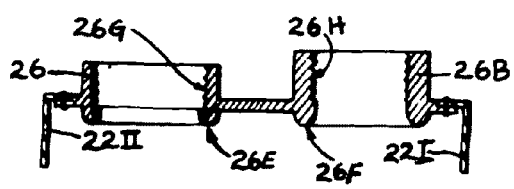
FIG. 19 is a cross-sectional view of a valve mounting body assembly of this present invention.

In reference to FIG. 19, tubular valve coupling bodies are represented by 26 and 26B which have threaded inner diametrical walls 26H and 26G respectively. 26E and 26F represent the rounded off bottom edges of the aforementioned valve coupling bodies 26 and 26B. The reinforcing inserts are represented by 22I and 22II. FIG. 19 is taken along line D-D1 of FIG. 15.

Figure 20:
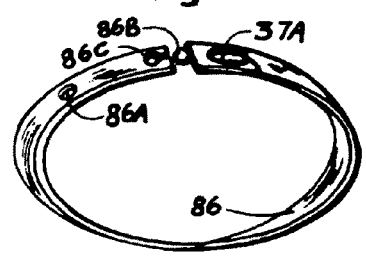
FIG. 20 is a perspective view of an adhesive backed strip (belt) for increasing the coupling strength of the left and right side heart members in both the vertical and horizontal directions.

In reference to FIG. 20, 37A represents an opening through which venting of warm air within the heart is accomplished. 86A is a hole for passing wires. 86B mates and interlocks with the hole 86C. 86 represents the adhesive-backed belt for strengthening the heart in a vertical or horizontal direction.

Figure 21:
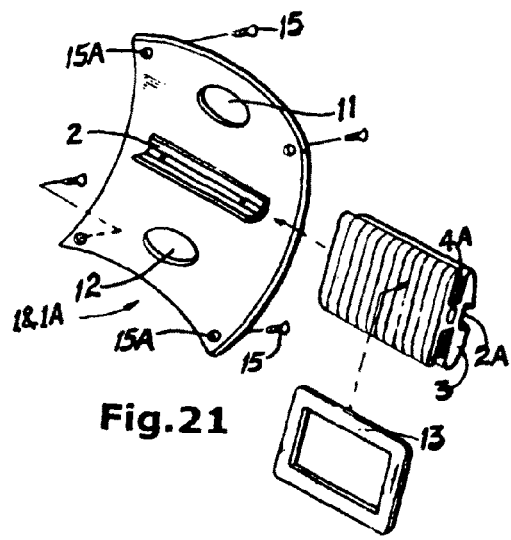
FIG. 21 is an exploded view of a-ventricle solenoid actuator (outer), and coupling plate.

In reference to FIG. 21, an outer actuator coupling plate 1 or 1A has air vents 11 and 12, as well as the mounting holes 15A for securing screws 15. The coil 4A is wound on the core 3 which is provided with a groove 2A which matches and mates with a securing stud 2. A resilient, thin foam material 13 bonded to the core 3 serves as a damping means for the moving diaphragm.

Figure 22:
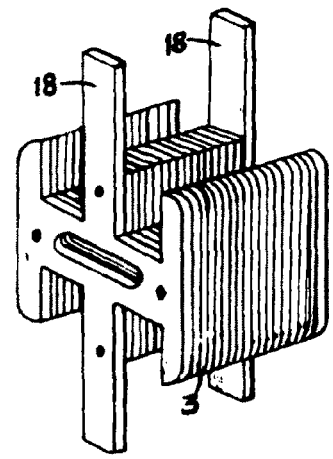
FIG. 22 is a perspective view of the median solenoid actuator core for auricles or ventricles.

In reference to FIG. 22, the median core structure 3, has the same basic design for both the auricles and the ventricles. On either side are the mounting posts 18 bonded or riveted to iron sheets constituting said Core 3.

Figure 23:
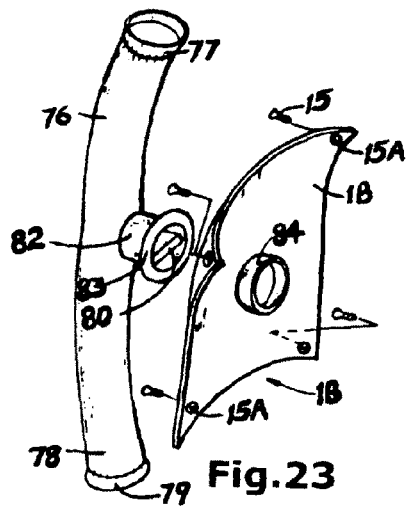
FIG. 23 is a perspective view showing the components of the vena cava system according to this present invention, and method of attaching the coupling plate 1B.

Referring now to FIG. 23, the vena cava system is comprised of the superior vena cava 76, the inferior cava 78. Both have flared entry mouths 77 and 79 respectively. Integrally molded to the aforesaid vena cava is a short connecting tube 82 with a flared exit lip 83. A central dividing wall 80 keeps both flows separate until they empty into the right auricle. This arrangement prevents the greater force of flow of the superior vena cava (thanks to gravity), from reducing the efficiency of the inferior vena cave. The flared lip 83 is pushed through the hole on the matching short tube 84 on the coupling plate 1B and bonded thereon. The said coupling plate is provided with mounting holes 15A for accepting the screws 15.

Figure 23A:
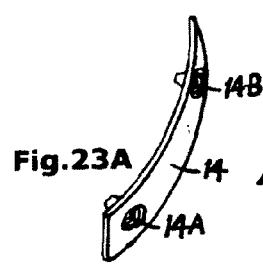
FIG. 23A is a perspective view of a threaded insert for attaching coupling plates to the heart.

FIG. 23A refers to an insert 14 for attaching the upper end of an auricle coupling plate or the lower end of a ventricle coupling plate to the heart. It is preferably made of a thin steel, aluminum or plastic material. It has two holes 14A and 14B which may or may not be threaded depending on the thickness of the material, for the purpose of catching mounting screws shown in (FIG. 21, 23 or 24).

Figure 24:
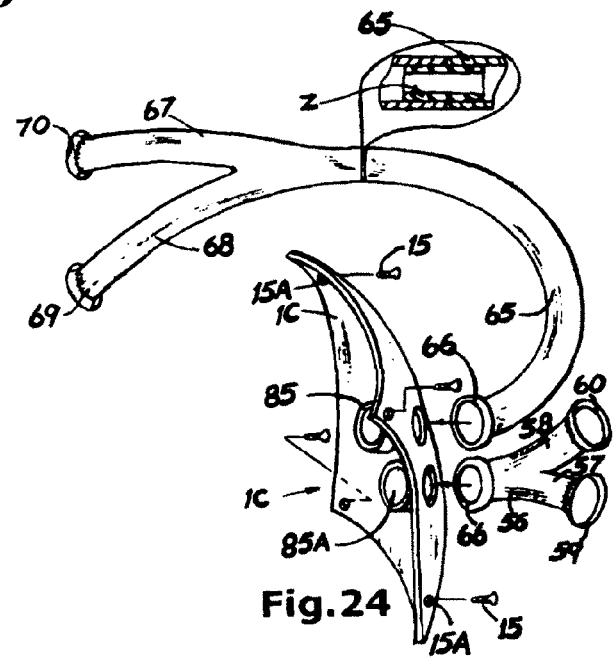
FIG. 24 is a perspective view of the left superior and left inferior pulmonary veins and method of attaching them to the coupling plate 1C.

In reference to FIG. 24, the two pulmonary veins are 56 and 65 which respectively bifurcate into the vessels 57, 58 and 67, 68. The flared exit mouths 59, 60, 69 and 70 are used to attach to natural vessels of the lungs. However, an adapter Z can be used to create a large single flared mouth 70A for example, thereby enabling connections to natural vessels to be made at points with larger diameters before small bifurcations. The coupling plate of the left auricle IC is provided with the short tubular holes 85 and 85A for accepting the matching flared lips 66 of the vessels 56 and 66 and are bonded thereon. Mounting holes 15A and the shown screws 15 are used to attach the assembly to the heart.

In reference to FIG. 25, 3 represents the iron sheets (core) of the actuating solenoids 4A, B, C, and D. 5 represents the moving magnets confronting the said cores 3. The arrows show that the Magnets move towards each other in the ventricles VL and VR of FIG. 1 as they repel away from their respective solenoids. The solenoids and magnets are configured in such a manner that, as the said magnets 5 dynamically move away from the said cores 3 and towards each other, they do not attract nor have enough holding torque to prevent effective responsive return to their rest positions. In other words, during the compression of the ventricular chambers, the solenoids must present enough repulsive force to overcome at all times, varying resisting loads presented by the blood returning from the auricles and elsewhere in the system, as well as the counteracting repulsive forces that are presented by like poles of the magnets 5 moving towards each other tending to oppose compression with increasing excursion distances of said diaphragms. It therefore entails a fine balance between electromagnetic and permanent magnetic forces. Opposing polarity arrangements of the magnets 5 eliminates the danger of attraction under any circumstance which could degrade and/or bring pumping action to a halt. This arrangement ensures rapid return of the diaphragms to their rest positions before the next cycle commences. It will be emphasized here, that if the magnets 5 are too powerful, then large amounts of electric power will be required by the solenoids to overcome their mutual repulsive resistance. On the other hand if the magnets 5 are weak and the solenoids are very powerful owing to large coils, thermal losses will inevitably increase and reduce efficiency of the system as well as increasing the risk of heating up the blood. Computer modeling may be used to determine the appropriate variables for both the magnets 5 and their solenoids.

Prior Art heart valve prostheses essentially falls into two basic categories namely, Mechanical heart valves (MHVs) and Biological heart valves (BHVs). All mechanical heart valves in current use worldwide engender promotion of thrombogenic events in the blood stream owing to, but not excessively limited to, large shear stresses, flow separation and stagnation. The net result of these events is the exposure of tissue factor, activation of blood platelets and/or foreign material contact activation which then leads to steps of initiation, amplification and propagation. Because of the ability of mechanical heart valves to initiate thrombogenic activity in the blood, all individuals on mechanical heart valve implants must take anti-coagulation medication for the rest of their lives. Mechanical heart valves on the positive side have proven to be reliable owing to their durability and improved blood flow, albeit with some degree of regurgitation. On the other hand, biological heart valves are essentially Xenographs, Allografts/autograts/isografts as exemplified in Porcine (pig) or Bovine (cow). In the Porcine example, the hearts from these animals are chemically treated, and then modified somewhat in order to make them implantable in humans. With Bovine or Equine (horse), the tissue from the pericardial sac is obtained and used to make the valve leaflets. The Porcine or Bovine heart valves are not as durable as mechanical heart valves but they possess all the benefits of the natural human heart which include but not limited to minimized blood regurgitation (backflow), efficient flow through the valve (low pressure gradients), non-thrombogenic activity initiating and being alive, are self-repairing, as well as exhibiting quick dynamic response profiles in response to abrupt changes in heart frequencies and contractile force. Though as aforementioned, biologic heart valves are usually not as durable as mechanical heart valves, they can have operating life spans exceeding 20 years, in addition to their aforesaid advantages over the mechanical heart valves. In conclusion, regarding the two valve types, i.e. MHVs and BHVs, when fully opened, the three leaflets of the human heart's ejection valves, i.e. pulmonary and aortic valves, simulate a convergent-divergent nozzle profile. In fluid dynamics theorem, this is a very efficient profile which has been employed in many products including loudspeaker enclosure ducts and aircraft engine exhaust nozzles. Also, all natural heart valve leaflets exhibit damping factor which is critical in negating blood vessel damage on closure during increased contractile forces by the heart. Mechanical heat valve designs do not engender true laminar flow profiles and possess little or no damping factor on closure, thereby resulting in their tendency to initiate thrombogenic activity by damaging blood cells.

Mechanical heart valve types include, but are not limited to, ball and cage (the first), Bi-leaflet, Tri-leaflet or pivoting disk. The most notable manufacturers of MHVs include St. Jude Medical, CarboMedics, TTK Chitra, ATS Medical, Baxter Edwards and Medtronic Hall Inc. The two valve designs for the present non-natural heart, i.e. single disk receiving valve and tri-leaflet ejection valves, attempt to duplicate some of the advantages of both the MHVs and the BHVs, i.e. reliability and durability as well as reduced tendency to initiate thrombogenic activity. This is made possible by single and tri-leaflet valve designs which exhibit damping factor on closing. Also, the present tri-leaflet design when fully opened, exhibits a convergent-divergent like profile which enhances laminar flow and reduces orifice pressures. Laminar flow is more critical in the ejection valves than in the receiving valves which only have to move blood into the ventricles. Also, though the present valves are passive and ultimate closure is effected by the blood pressure, they do possess some degree of self closure. These are some of the notable advantages of the present valve designs to those of the prior art, which are well known worldwide.

Figure 26:
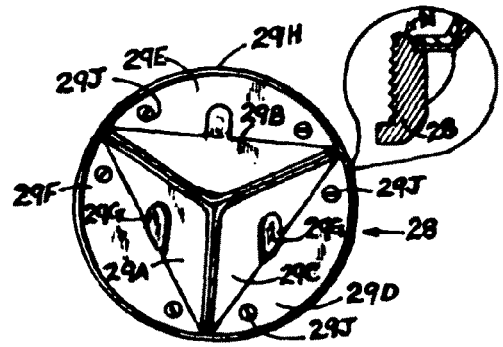
FIG. 26 is a top view of a tri-leaflet ejection valve in accordance with this present invention.

FIG. 25 shows proper magnetic orientation of the drive units*. Referring now to FIG. 26, as with the natural heart, the ejection valves 28 have three leaflets 29A, 29B and 29C which are held in place by means of mounting plates 29D, 29E and 29F and screws 29J. The stops 29N (see FIG. 29) are covered with a rubber damper 29G and are set at about an angle of about 68° to minimize maximum stretching of the diaphragm materials at the pivot point. The outer diametrical edge 29H is threaded for the purpose of coupling to the pulsating units (see FIGS. 11 and 12). All components fall within and below the rounded edge W (enlarged area) of valve body 28.

Figure 27:
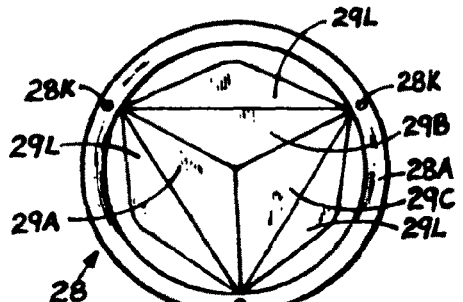
FIG. 27 is a bottom view of a tri-leaflet ejection valve in accordance with this present invention.

In reference to FIG. 27, the leaflets are represented by 29A, 29B and 29C. The leaflets are mounted with screws on the ledges 29L. An edge flange 28A is provided with small holes 28K for accepting a special tool for mounting the valve 28 on the appropriate pulsating unit's housing.

Figure 28:
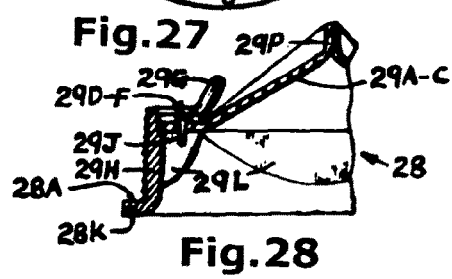
FIG. 28 is a cross-sectional view of a tri-leaflet ejection valve according to the teachings of this present invention.

Now referring to FIG. 28, the ejection valve 28 has a threaded radial edge 29H and a lower edge flange 28A provided with holes 28K for the purpose of accepting a special tool for mounting unto an appropriate pulsating unit's housing. The leaflets 29A-C have a cusp-like upper edge 29P and flat mounting plates 29D-F for the purpose of mounting with screws 29J atop the ledges 29L. Integral with the said mounting plates 29D-F is a stop cover with a damping material 29G which sets the maximum excursion angle of the aforesaid leaflets 29A-C.

Figures 29, 30:
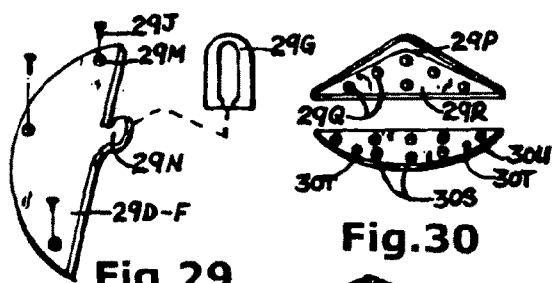
FIG. 29 is a view of a stationary leaflet member for a tri-leaflet ejection valve and damping material.
FIG. 30 shows the reinforcing perforated leaflet members for a tri-leaflet ejection valve according to this present invention.

Now referring to FIG. 29, the securing plates 29D-F are provided with holes 29M for accepting the screws 29J as well as an integral stop 29N. A silicone rubber piece 29G slips unto the stop 29N and serves as a damping means.

Now referring to FIG. 30 the reinforcing members for a tri-leaflet diaphragm valve is composed of the movable insert piece 29R having a raised cusp-like edge 29P that terminates towards the sides. It is provided with perforations 29Q so that the encapsulating molding material can flow through and interlock. The non-movable insert piece 30U is also provided with perforations 30S for interlocking with the encapsulating molding material. It is also provided with additional holes 30T aligned with those on the mounting ledges 29L (see FIG. 28) which permit the securing screws to be employed.

Figure 31:
FIG. 31 is a tri-leaflet ejection valve strengthening mesh insert member in accordance with this present invention.

Referring now to FIG. 31, the reinforcing cloth mesh 29S for tri-leaflets can be made from nylon, Dacron, Kevlar or other appropriate material. It is trimmed to match and mate with the reinforcing perforated inserts 29R (moving) and 30U (non-moving) shown in FIG. 30, in such a manner as to permit low fluid pressures to movably open or close the leaflets along the axis of pivot that seperates both said inserts.

Figure 32:
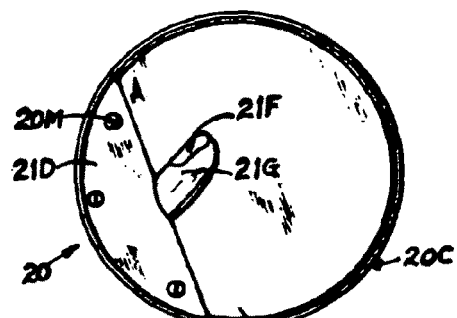
FIG. 32 is a top view of a mono-leaflet receiving valve in accordance with this invention.

In reference to FIG. 32 the single leaf valve 20 has threaded coupling edge 20C, a diaphragm leaf 21, a diaphragm mounting plate 21D provided with matching holes for screws 20M. The mounting plate 21D has an integral stop piece 21F covered with a rubber cap 21G for damping when contact is made with the diaphragm 21 during maximum excursions. It is preferably set at an angle of about 68°. This angle keeps maximum stretching of moving diaphragm members at reasonable levels while presenting enough opening of the leaflets at maximum loads. However, various angles are possible.

Figure 33:
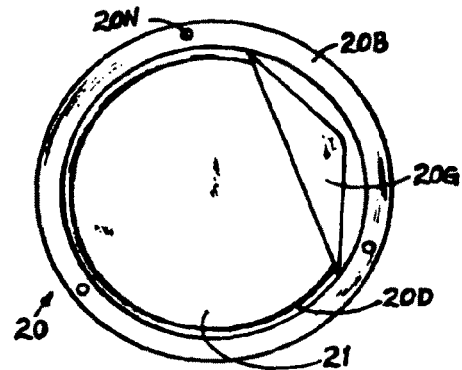
FIG. 33 is a bottom view of a mono-leaflet receiving valve in accordance with this present invention.

In reference to FIG. 33, the single leaf valve 20 seen from bottom view has an outer edge mounting flange 20B, diaphragm 21, a lower diaphragm stop 20D having a half moon configuration, a diaphragm mounting ledge 20G and holes 20N for accepting a special tool for coupling to a valve mounting body 26 or 26A on the ventricles VR and VL as shown in FIG. 15.

Figure 34:
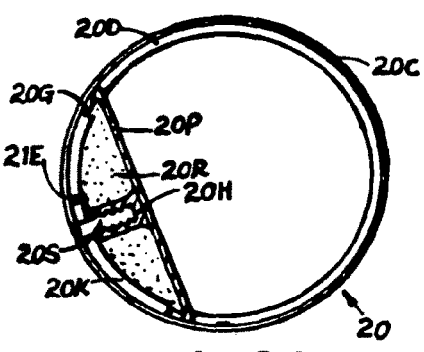
FIG. 34 is a cross-sectional view taken from the top, of a mono-leaflet receiving valve without the diaphragm, in accordance with the teaching of this present invention.

Referring now to FIG. 34, the single leaf valve 20 shown with diaphragm and components removed, has a threaded edge 20C, a lower diaphragm stop 20D, diaphragm mounting ledge wall 20P having a threaded stem 20H for accepting a securing screw 20S, and flanged ears 20G that snugly fit between aforesaid lower diaphragm stop 20D and a seat 20K having a hole 21E for accepting a screw that rigidly secures a top piece 20L (FIG. 38) of diaphragm mounting ledge wall 20P as well as a mounting plate 21D (FIG. 32) to the valve body seat 20K. The cavity created between the wall of the ledge 20P and the inner valve body is filled with either silicone or foam 20R to reduce tendency of said ledge wall 20P to flex without significantly increasing weight. However, 20P and 20H can be integrally molded with the rest of the valve body.

Referring to FIG. 35, the single leaf diaphragm 21 shown is designed according to the teachings of this present invention and is comprised of a thin perforated movable insert member 21A having said perforations 21B, a non-movable, perforated insert member 21D, a reinforcing open cell type cloth mesh 21C and holes 21E that run through the molding material of the diaphragm 21E and aforesaid non-movable insert member 21D for coupling to the valve body. The pivot axis is along line E-E1. Inset shows how a bulged edge lip 21K of silicone deposit sits on the valve seat 20D to increase damping factor on closure, so as to reduce damage to blood cells.

Referring to FIG. 36, the diaphragm securing plates 21D is provided with holes 21E for accepting the appropriate screws for rigidly attaching the diaphragm to the valve body. A stop 21F is integral with the plate and is covered with a silicone rubber material 21G which serves as a force damping means.

In reference to FIG. 37, the perforated thin metal insert 21A is provided with said perforations 21B and serves to reinforce the movable section of the diaphragm.

Referring to FIG. 38, the hollow diaphragm mounting ledge 20Q forms into ears 20G. It has a threaded stem 20H for positioning and steadying it within the valve by means of screws. The ledge Flange 20L is provided with mounting holes 20E. The ledge wall is represented by 20P.

Now referring to FIG. 39, a cross-sectional view of the hollow ledge 20Q shows that the threaded stem 20H is integral with the wall 20P and is also provided with threaded stems 20E as well, for accepting screws 20M. The ledge flange is represented by 20L.

Now referring to FIG. 40, the receiving valve 20 is provided with an edge flange 20B, a threaded outer diametrical wall 20C for coupling to the housing of a pulsating unit. The inner wall has a diaphragm stop 20D and a diaphragm ledge seat 20K. A threaded hole 20F is for attaching aforesaid diaphragm ledge.

In reference to FIG. 41, the receiving valve 20 is provided with an edge flange 20B, a threaded outer diametrical wall 20C, a single leaf diaphragm 21, a diaphragm securing plate 21D having a stop and a damping means 21G, said securing plate and connecting assembly being rigidly secured to the valve body by means of locking nut 20S and securing screws 21H. The maximum angle achieved by the diaphragm 21 as defined by the dotted lines 21J is set by the stop 21G.

In reference to FIG. 42, the multi pin plugs fit into matching round sockets 87 and carry signals to and from the controller 61. The wires 48, however, could always be coupled to plugs of various designs. Plugs permit easy surgical removal/replacement of the controller when the need arises.

Referring now to FIG. 43, this modification of the vena cava system shows front and side views of the superior vena cava 76 and inferior vena cava 78. The said vessels maintain their normal rounded cross-sections towards the flared entry mouths 77 and 79. However, the vessels increase in width but reduce in depth while taking the curvature of the right auricle AR at the point of attachment shown in FIG. 1. Also, the short connecting tube 82 having a flared lip 83 and a central dividing wall 80 assume a matching profile. Also, the coupling plate 1B having an exit tube 84 matches and mates with the component members of the vena cava system. This arrangement permits a larger total surface area of the vessels without substantially increasing the overall size of the heart.

I claim:

1. A wholly implantable non-natural heart system for humans, comprising:
    a pumping unit; and
    a power supply module and a controller;
    wherein the pumping unit comprises:
        a chassis comprising a flat central web with end flanges and four holes configured to accept tubular valve mounting bodies embedded in a mass of heart material;
        left and right heart halves bondably attached to coupling flanges for reinforcement;
        wherein the left and right heart halves comprise left and right auricles and left and right ventricles comprising one-way valves, rigidly coupled to valve mounting bodies, for the purpose of controllably moving blood into and from the circulation system;
        solenoid actuators comprising diaphrams at the edges of the auricles and ventricles; and
        Aortic and Pulmonic system pulsating units rigidly coupled to valve mounting bodies connected to the left ventricle and to the right ventricle, respectively, wherein the pulsating units enhance overall efficiency of a resulting pumping action by recoil;
    wherein the diaphrams of the solenoid actuators move and cause compression and relaxation of the chambers of the auricles and ventricles, the resulting blood pressures in the auricles and ventricles passively manipulating the valves;
    wherein the solenoid actuators are supplied with electrical power from the power supply module and controller;
    wherein the diaphragms comprise integral yieldable annular surrounds that permit only axial motions in a pistonic manner, such that rhythmic opening and closing of the one-way valves moves blood into the Pulmonic and Aortic system pulsating units;
    wherein lung vessels are attached to a rigid coupling plate that is in turn bonded to the left auricle, such that the oxygen rich blood of the lung vessels empties into the left auricle, thereby moving blood to and from the lungs;
    wherein a second auricle coupling plate is bonded to the right auricle and connects a vena cava system to said right auricle.

2. The wholly implantable non-natural heart of claim 1, further comprising an adhesive-backed belt bonded along a seam defining the left and right halves of the heart and reduces the risk of separation of the individual chambers from the others owing to the torsional forces produced by the actuators.

3. The wholly implantable non-natural heart of claim 1, further comprising temperature and pressure sensors mounted in the aorta, a mechanical overpressure switch, and cuff electrodes connected to the sympathetic and parasympathetic trunks, wherein the controller receives and uses signals from the temperature and pressure sensors and mechanical overpressure switch and nerve input signals retrieved via the cuff electrodes to modify the output of the solenoid actuators and manipulate frequency and contractile force of pumping instantaneously.

4. The wholly implantable non-natural heart of claim 3, wherein the mechanical overpressure switch is a part of the Aortic system pulsating unit and is a cantilever or axial travel mechanical switch.

5. The wholly implantable non-natural heart of claim 4, wherein the mechanical overpressure switch introduces electrical resistance via resistors in a controlling circuit, thereby effectively modifying dangerous excessive pressure gradients when they occur.

6. The wholly implantable non-natural heart of claim 3, wherein the temperature and pressure sensors are probe or diaphragm sensors.

7. The wholly implantable non-natural heart of claim 1, wherein the valves are single or tri-leaflet valves.

8. The wholly implantable non-natural heart of claim 1, wherein wherein the diaphragms of the solenoid actuators are driven by flat magnets interacting with electronmagnet stators.

9. The wholly implantable non-natural heart according to claim 1, in which the pumping unit is configured to be implanted in its natural position above the diaphragm, and the controller, behind the breastbone and the power module in the lower abdomen, such that each can be removed and replaced during a surgical operation if need be, without affecting the others.

10. The wholly implantable non-natural heart for humans according to claim 1, wherein the coupling flanges comprise an auricle's coupling flange, which aids the auricles in resisting torsional divergence presented by unbalanced actuator outputs from the left and right sides, and a ventricle's coupling flange which aids the ventricles in resisting torsional divergence presented by unbalanced actuator outputs from the left and right sides.

11. The wholly implantable non-natural heart for humans according to claim 1, in which the Aortic pulsating units' housing is coupled to its valve mounting body so as to present an effective blood seal between the left auricle and left ventricle thereon and the Pulmonic pulsating units' housing is coupled to its valve mounting body so as to present an effective blood seal between the right auricle and right ventricle thereon.

12. The wholly implantable non-natural heart for humans according to claim 1, in which the valves are coupled to their respective valve mounting bodies such that in each case an effective blood seal is presented between the auricles and ventricles thereon.

13. The wholly implantable non-natural heart for humans according to claim 1, wherein the yieldable surrounds are filled with a heat absorbing material for the purpose of absorbing some heat generated by the actuating solenoids.

14. The wholly implantable non-natural heart for humans according to claim 1, further comprising metal inserts embedded in heart material and configured to be connected by screws to coupling plates and the chassis.

15. The wholly implantable non-natural heart for humans according to claim 1, further comprising a wire harness comprising quick disconnect plugs leading to the controller, such that the controller can be easily and quickly removed and replaced if need be, after access has been gained surgically.

16. The wholly implantable non-natural heart for humans according to claim 1, wherein the diaphragms are driven by either moving magnets (MM) or moving coils (MC).

17. The wholly implantable non-natural heart for humans according to claim 1, wherein the solenoid actuators comprise moving magnets, wherein the magnets are oval, round, race track or square in shape.

18. The wholly implantable non-natural heart for humans according to claim 1, wherein the Pulmonic and Aortic system pulsating units are held firmly to Pulmonic and Aortic vessels, respectively, by a combination of bonding agents and spring clamps, wherein the spring clamps have rounded edges to negate damage to blood vessels.

19. The wholly implantable non-natural heart for humans according to claim 18, wherein the pulsating units comprise a stretchable membrane having a resilient foam backing configured to mimic natural arterial expansion and contraction during pumping.

20. The wholly implantable non-natural heart for humans according to claim 19, wherein a mechanical overpressure switch embedded within the Aortic system pulsating unit is configured such that excessive and dangerous arterial pressures cause the stretchable membrane and foam backing to movably close switch contacts, thereby introducing electronic countermeasures in the form of voltage/current reduction and increased resistance to the signals emanating via the controller and reaching the solenoid actuators, hence resulting in a reduction of said excessive pressures.

21. The wholly implantable non-natural heart for humans according to claim 3, wherein the temperature and pressure sensors are microprobe and diaphragm types respectively, wherein the temperature and pressure sensors are rigidly positioned on the aortic arch such that the temperature sensor extends into the Aorta and remains in constant contact with the blood and the pressure sensor extends into the Aorta as well, but is shrouded by heart material such that it has no direct contact with the blood, wherein the overpressure mechanical switch comprises a spring loaded, axially moving contact rigidly welded to a curved stop arm for contacting a stretchable membrane of the Aortic system pulsating unit, wherein the switch further comprises mounting flanges having mounting holes for rigidly mounting the unit to the housing of the Aortic system pulsating unit by means of screws.

22. The wholly implantable non-natural heart for humans according to claim 19, wherein the pulsating units comprise component housings provided with upper necks for attaching to the great vessels externally by means of bonding agents and clamps, wherein inner surfaces of the upper necks of the pulsating units comprise the stretchable membranes bondably attached thereon, and are held firmly by flat tension clamps, such that a curved portion of the inner surfaces of the upper housing necks are in continuous contact with the blood and are highly polished or coated with anticoagulants to prevent clotting of blood.

23. The wholly implantable non-natural heart for humans according to claim 1, further comprising a valve mounting body assembly connecting two or more valve mounting bodies for stability and ventricle coupling plates for coupling the ventricles to the chassis, wherein the coupling flanges comprise an auricles coupling flange and a ventricles coupling flange, wherein the coupling plates, coupling flanges, valve mounting body assembly and chassis comprise punched holes and kinking to reduce weight without compromising strength.

24. The wholly implantable non-natural heart for humans according to claim 1, wherein the yieldable surrounds are integral with the diaphragms of the actuators and with the rest of the heart material for each chamber, wherein the surrounds are reinforced by bonding with woven fibre cloth.

25. The wholly implantable non-natural heart for humans according to claim 24, wherein the surrounds are single or double roll convex, single or double roll concave, single or double V groove, flat annular design or an integral accordion configuration.

26. The wholly implantable non-natural heart for humans according to claim 1, wherein only repulsion of the magnets from the actuating solenoids is used to generate dynamic compressive forces for opening the valves and, in the case of the ventricles, to aid in the rapid return of the moving diaphragms to their rest positions in preparation for the next cycle.

27. A wholly implantable non-natural heart for humans according to claim 1, further comprising blood vessels made of bio-inert material comprising flared exit mouths for the purpose of attaching by suturing with natural human body blood vessels with varying diameters, wherein the flared exit mouths are made of a woven fabric to promote growth of body tissue into it, wherein the exit mouths are either integrally molded with the artificial vessels or attached by stitching or bonding with a suitable bonding agent.

28. The wholly implantable non-natural heart for humans according to claim 1, wherein the rigid coupling plates are encapsulated with a thin coat of silicone to further strengthen them and make them bio-compatible.

* * * * *